United States Patent
Nguyen et al.

(10) Patent No.: US 11,421,016 B2
(45) Date of Patent: Aug. 23, 2022

(54) CANCER NEOEPITOPES

(71) Applicants: NANTOMICS, LLC, Culver City, CA (US); Nant Holdings IP, LLC, Culver City, CA (US)

(72) Inventors: Andrew Nguyen, San Jose, CA (US); Kayvan Niazi, Agoura Hills, CA (US); Patrick Soon-Shiong, Los Angeles, CA (US); Shahrooz Rabizadeh, Los Angeles, CA (US); Stephen Charles Benz, Santa Cruz, CA (US)

(73) Assignees: NantOmics LLC, Culver City, CA (US); Nant Holdings IP, LLC, Culver City, CA (US)

( * ) Notice: Subject to any disclaimer, the term of this patent is extended or adjusted under 35 U.S.C. 154(b) by 935 days.

(21) Appl. No.: 15/568,487

(22) PCT Filed: Apr. 25, 2016

(86) PCT No.: PCT/US2016/029244
§ 371 (c)(1),
(2) Date: Oct. 23, 2017

(87) PCT Pub. No.: WO2016/172722
PCT Pub. Date: Oct. 27, 2016

(65) Prior Publication Data
US 2018/0141998 A1     May 24, 2018

Related U.S. Application Data

(60) Provisional application No. 62/159,145, filed on May 8, 2015, provisional application No. 62/178,956, filed on Apr. 23, 2015.

(51) Int. Cl.
| | |
|---|---|
| C07K 16/00 | (2006.01) |
| G16B 5/00 | (2019.01) |
| G16B 20/00 | (2019.01) |
| G16B 30/00 | (2019.01) |
| G16B 35/00 | (2019.01) |
| G16C 20/60 | (2019.01) |
| A61K 35/17 | (2015.01) |
| C07K 16/30 | (2006.01) |
| C07K 16/32 | (2006.01) |
| C12Q 1/6886 | (2018.01) |
| G16B 20/30 | (2019.01) |
| G16B 20/20 | (2019.01) |
| G16B 35/20 | (2019.01) |
| G16B 20/50 | (2019.01) |
| A61P 35/00 | (2006.01) |
| A61K 38/17 | (2006.01) |
| A61K 39/00 | (2006.01) |
| A61K 39/395 | (2006.01) |
| A61K 45/00 | (2006.01) |
| C07K 14/735 | (2006.01) |

(52) U.S. Cl.
CPC ............ *C07K 16/005* (2013.01); *A61K 35/17* (2013.01); *A61K 38/1774* (2013.01); *A61K 39/0011* (2013.01); *A61K 39/39558* (2013.01); *A61K 45/05* (2013.01); *A61P 35/00* (2018.01); *C07K 14/70535* (2013.01); *C07K 16/30* (2013.01); *C07K 16/32* (2013.01); *C12Q 1/6886* (2013.01); *G16B 5/00* (2019.02); *G16B 20/00* (2019.02); *G16B 20/20* (2019.02); *G16B 20/30* (2019.02); *G16B 20/50* (2019.02); *G16B 30/00* (2019.02); *G16B 35/00* (2019.02); *G16B 35/20* (2019.02); *G16C 20/60* (2019.02); *A61K 2039/505* (2013.01); *A61K 2039/55* (2013.01); *A61K 2039/585* (2013.01); *C07K 2317/32* (2013.01); *C07K 2317/34* (2013.01); *C07K 2317/622* (2013.01); *C07K 2317/92* (2013.01); *C12Q 2600/106* (2013.01); *C12Q 2600/156* (2013.01); *C12Q 2600/158* (2013.01)

(58) Field of Classification Search
None
See application file for complete search history.

(56) References Cited

U.S. PATENT DOCUMENTS

| | | | |
|---|---|---|---|
| 7,473,532 | B2 | 1/2009 | Darfler et al. |
| 8,207,315 | B2 | 6/2012 | Wang et al. |
| 8,652,473 | B2 | 2/2014 | Johns et al. |
| 2005/0048070 | A1 | 3/2005 | Ditzel et al. |
| 2010/0202968 | A1 | 8/2010 | Nitsch |

(Continued)

FOREIGN PATENT DOCUMENTS

| | | |
|---|---|---|
| CA | 2 987 730 A1 | 10/2016 |
| CA | 2 988 388 A1 | 10/2016 |
| CN | 102504024 A | 6/2012 |
| CN | 103384887 A | 11/2013 |
| CN | 108513593 A | 9/2018 |

(Continued)

OTHER PUBLICATIONS

Carter, Paul, "Improving The Efficacy of Antibody-Based Cancer Therapies," Nature Reviews (Cancer), vol. 1, pp. 118-129 (Nov. 2001).

(Continued)

*Primary Examiner* — Michael L Borin
(74) *Attorney, Agent, or Firm* — Martin Fessenmaier; Umberg Zipser LLP (57) ABSTRACT

Contemplated compositions and methods are directed to cancer neoepitopes and uses of such neoepitopes, especially to generate synthetic antibodies against neoepitopes that may then be employed in the manufacture of a therapeutic agent. Preferred therapeutic agents will comprise a synthetic antibody against a neoepitope, and most preferably in combination with a cellular or non-cellular component for use as a diagnostic or therapeutic agent.

17 Claims, 2 Drawing Sheets
Specification includes a Sequence Listing.

(56) References Cited

U.S. PATENT DOCUMENTS

| | | | |
|---|---|---|---|
| 2010/0203109 A1 | 8/2010 | Herlyn | |
| 2011/0293637 A1 | 12/2011 | Hacohen et al. | |
| 2012/0059670 A1* | 3/2012 | Sanborn | G06F 19/00 705/3 |
| 2012/0066001 A1* | 3/2012 | Sanborn | G06N 7/005 705/3 |
| 2015/0125463 A1 | 5/2015 | Cogswell et al. | |
| 2016/0101170 A1 | 4/2016 | Hacohen et al. | |
| 2018/0142016 A1* | 5/2018 | Wong | A61K 51/1027 |
| 2018/0147294 A1* | 5/2018 | Jackson | A61K 31/454 |
| 2019/0070308 A1* | 3/2019 | Goldenberg | A61K 47/6859 |
| 2019/0099475 A1 | 4/2019 | Benz et al. | |

FOREIGN PATENT DOCUMENTS

| | | |
|---|---|---|
| EP | 2 279 749 A1 | 2/2011 |
| EP | 3 280 738 A1 | 2/2018 |
| EP | 3 286 361 A1 | 2/2018 |
| JP | 2018513187 A | 5/2018 |
| MX | 2017013613 A | 9/2018 |
| WO | 0158956 A2 | 8/2001 |
| WO | 2011/143656 A2 | 11/2011 |
| WO | 2011/143656 A3 | 8/2012 |
| WO | 2014-052707 A2 | 4/2014 |
| WO | 2015/058159 A1 | 4/2015 |
| WO | 2015095811 A2 | 6/2015 |
| WO | 2015103037 A2 | 7/2015 |
| WO | 2016/164833 A1 | 10/2016 |
| WO | 2016/172722 A1 | 10/2016 |

OTHER PUBLICATIONS

Fritsch, et al., "HLA-Binding Properties of Tumor Neoepitopes in Humans," Cancer Immunology Research, vol. 2, No. 6, Jun. 2014, 9 pages.
ISA/KR, International Search Report and Written Opinion, completed Aug. 9, 2016 for PCT Application No. PCT/US2016/029244, 15 pages.
Alexandrov et al. "Signatures of mutational processes in human cancer", Nature, 2013, vol. 500, pp. 415-421.
Dung T. Le et al., "PD-1 Blockade in Tumors with Mismatch-Repair Deficiency", The New England Journal of Medicine,—NEJM—, US, (Jun. 25, 2015), vol. 372, No. 26, doi:10.1056/NEJMoa1500596, ISSN 0028-4793, pp. 2509-2520.
E. M. Van Allen et al, "Genomic correlates of response to CTLA-4 blockade in metastatic melanoma", Science, US, (Oct. 9, 2015), vol. 350, No. 6257, ISSN 0036-8075, pp. 207-211.
First Office Action received for Australian Patent Application Serial No. 2016339035, dated Nov. 6, 2019, 04 pages.
Snyder et al., "Genetic basis for clinical response to CTLA-4 blockade in melanoma", New England Journal of Medicine, (2014), vol. 371, No. 23, pp. 2189-2199.
Carreno, B.M., et al. Supplementary Materials for A dendritic cell vaccine increases the breadth and diversity of melanoma neoantigen-specific T cells, Science Express, Apr. 2, 2015, pp. 1-27.
Matsushita, H., et al.. Cancer exome analysis reveals a T-cell-dependent mechanism of cancer immunoediting, Nature, Feb. 2012, pp. 400-404, vol. 482.
Reuschenback, M., et al., A multiplex method for the detection of serum antibodies against in silico-predicted tumor antigens, Cancer Immunol Immunother, Aug. 21, 2014, pp. 63:1251-1259.
Carreno, B. M. et al., A dendritic cell vaccine increases the breadth and diversity of melanoma neoantigen-specific T cells, Cancer Immunotherapy, May 15, 2015, pp. 803-808, vol. 348.
Notice of acceptance received for Australian Patent Application Serial No. 2016253145 dated Jun. 18, 2020, 3 pages.
Office Action received in Canadian Patent Application Serial No. 2988388 dated May 19, 2020, 4 pages.
Notice of Reasons for Refusal received for Japanese Patent Application Serial No. 2017555492 dated Apr. 14, 2020, 6 pages (Including English Translation).

Schietinger et al., "A Mutant Chaperone Converts a Wild-Type Protein into a Tumor-Specific Antigen", Science, 2006, vol. 314, pp. 304-308.
Ito et al., "Molecular Designs of Antibodies and Peptides by Phage Display", Biophysics, 2008, vol. 48, No. 5, 8 pages.
Wang et al., "Overexpression of AGGF1 is correlated with angiogenesis and poor prognosis of hepatocellular carcinoma", Medical Oncology, Mar. 22, 2015, vol. 32, No. 131, 9 pages.
Tian et al., "Identification of an angiogenic factor that when mutated causes susceptibility to Klippel-Trenaunay syndrome", Nature, Feb. 12, 2004, vol. 427, pp. 640-645.
Lutz et al., "Can we predict mutant neoepitopes in human cancers for patient-specific vaccine therapy?", Cancer Immunology Research, Jun. 2014, vol. 2, No. 6, pp. 1-5.
Fritsch et al., "Personal neoantigen cancer vaccines: The momentum builds", Oncolmmunology, Jun. 2014, vol. 3, 4 pages.
International Search Report and Written Opinion received for PCT Application Serial No. PCT/US2016/026798 dated Jul. 18, 2016, 14 pages.
Parmiani et al., "Integrating Immune Checkpoint Blockade with Anti-Neo/Mutated Antigens Reactivity to Increase the Clinical Outcome of Immunotherapy", Vaccines, 2015, vol. 3, pp. 420-428.
Rooij et al., "Tumor Exome Analysis Reveals Neoantigen-Specific T-Cell Reactivity in an Ipilimumab-Responsive Melanoma", Journal of Clinical Oncology, Nov. 10, 2013, vol. 31, No. 32, pp. e439-e442.
Castle et al., "Exploiting the Mutanome for Tumor Vaccination", Cancer Research, Mar. 1, 2012, vol. 72, No. 5, pp. 1081-1091.
Hacohen et al., "Getting Personal with Neoantigen-Based Therapeutic Cancer Vaccines", Cancer Immunology research, Jul. 2013, vol. 1, No. 1, p. 1-8.
Lundegaard et al., "NetMHC-3.0: accurate web accessible predictions of human, mouse and monkey MHC class I affinities for peptides of length 8-11", Nucleic Acids Research, 2008, vol. 36, pp. W509-W512.
Kelderman et al., "Mismatch Repair-Deficient Cancers Are Targets for Anti-PD-1 Therapy", Cancer Cell, Jul. 13, 2015, vol. 28, pp. 11-13.
Charoentong et al., "Bioinformatics for cancer immunology and immunotherapy", Cancer Immunol Immunother, 2012, vol. 61, pp. 1885-1903.
Rizvi et al., "Mutational landscape determines sensitivity to PD-1 blockade in non-small cell lung cancer", Cancer Immunology, Science, Apr. 3, 2015, vol. 348, No. 6230, pp. 124-128.
Segal et al., "Epitope Landscape in Breast and Colorectal Cancer", Cancer Research, Feb. 1, 2008, vol. 68, No. 3, pp. 889-892.
Sykulev et al., "Evidence that a Single Peptide-MHC Complex on a Target Cell Can Elicit a Cytolytic T Cell Response", Immunity, Jun. 1, 1996, vol. 4, No. 6, pp. 565-571.
Kim et al., "HLA Haplotyping from RNA-seq Data Using Hierarchical Read Weighting", PLoS One, Jun. 2013, vol. 8, No. 6, pp. 1-10.
Warren et al., "Derivation of HLA types from shotgun sequence datasets", Genome Medicine, 2012, vol. 4, No. 12, pp. 1-8.
Liu et al., "ATHLATES: accurate typing of human leukocyte antigen through exome sequencing", Nucleic Acids Research, Jun. 8, 2013, vol. 41, No. 14, pp. 1-8.
Bai et al., "Inference of high resolution HLA types using genome-wide RNA or DNA sequencing reads", BMC Genomics, 2014, vol. 15, No. 325, pp. 1-16.
Amalfitano et al., "Production and Characterization of Improved Adenovirus Vectors with the E1, E2b, and E3 Genes Deleted", Journal of Virology, Feb. 1998, vol. 72, No. 2, pp. 926-933.
Vigneron et al., "Database of T cell-defined human tumor antigens: the 2013 update", Cancer Immunity, Jul. 15, 2013, vol. 13, 6 pages.
Carmen et al., "Concepts in antibody phage display", Briefings in Functional Genomics and Proteomics, Jul. 2002, vol. 1. No. 2, pp. 189-203.
Hosse et al., "A new generation of protein display scaffolds for molecular recognition", Protein Science, Jan. 2006, vol. 15, No. 1, pp. 14-27.
First Office Action received for Canadian Patent Application Serial No. 2987730 dated Jul. 31, 2018, 06 pages.

(56) References Cited

OTHER PUBLICATIONS

Second Office Action received for Canadian Patent Application Serial No. 2987730 dated Feb. 25, 2019, 04 pages.
Haisma H.J, "Monoclonal antibodies and cancer: Studies on the use of monoclonal antibodies for imaging and therapy of cancer, with a special emphasis on ovarian carcinoma", Dec. 8, 1957, 175 pages.
Gubin et al., Tumor neoantigens: building a framework for, personalized cancer immunotherapy, The Journal of Clinical Investigation, Sep. 2015, vol. 125, No. 9, pp. 3413-3421.
Srivastava P.K, "Neoepitopes of Cancers: Looking Back, Looking Ahead", Cancer Immunology Research, Sep. 1, 2015, vol. 3, No. 9, pp. 969-977.
Monteiro J, "Cancer Immunotherapy Scores Again", Cell, Jan. 15, 2015, vol. 160, p. 7-9.
Hundal et al., "pVAC-Seq: A genome-guided in silica approach to identifying tumor neoantigens", Genome Medicine, Jan. 29, 2016, vol. 8, No. 11, p. 1-11.
Akkawi et al., "The human VG5Q gene 2 transcript is over-expressed in colorectal and bladder carcinomas", Gene Therapy Molecular Biology, 2006, vol. 10, pp. 173-178.
Supplementary European Search report received for European Patent Application Serial No. 16777432 dated Aug. 29, 2018, 03 pages.
Rabizadeh et al., "Comprehensive genomic transcriptomic tumor-normal gene panel analysis for enhanced precision n patients with lung cancer", Oncotarget, Apr. 2018, vol. 9, No. 27, pp. 19223-19232.
Extended European Search report received for European Patent Application Serial No. 16784102.2 dated Apr. 5, 2019, 13 pages.
International Preliminary Report on Patentability received for PCT Application Serial No. PCT/US2016026798 dated Oct. 10, 2017, 01 pages.
Herbst et al., "Predictive correlates of response to the anti-PD-L1 antibody MPDL3280A in cancer patients", Nature, Nov. 27, 2014, vol. 515, pp. 1-18.
First Office Action received for Russian Patent Application Serial No. 2017145136/10(077299) dated Sep. 13, 2019, 14 pages (Including English Translation).
Extended European Search report received for European Patent Application Serial No. 16777432.2 dated Nov. 30, 2018, 11 pages.
Non-Final office Action Received for U.S. Appl. No. 15/565,203, dated Jun. 18, 2019, 17 pages.
International Preliminary Report on Patentability Chapter II received for PCT Application Serial No. PCT/US2016/029244 dated Aug. 22, 2017, 18 pages.
First Examination report received for Australian Patent Application Serial No. 2016253145, dated Jan. 17, 2020, 05 pages.
Communication Pursuant to rule 164(1) EPC received in European Patent Application Serial No. 16784102.2, dated Jan. 3, 2019, 15 pages.
Office Action received for Canadian Patent Application Serial No. 2,988,388 dated Apr. 7, 2021, 3 pages.
Office Action received for Mexico Patent Application Serial No. MX/a/2017/013613 dated Jul. 6, 2021, 8 pages. (Including English Translation).
Second Office Action received for Chinese Patent Application Serial No. 201680037507.1 dated Jul. 20, 2021, 15 pages. (Including English Translation).
Office Action received for Mexico Patent Application Serial No. MX/a/2017/013613 dated Nov. 19, 2021, 8 pages. (Including English Translation).
Decision of Refusal received for Japanese Patent Application Serial No. 2017-555492 dated Dec. 22, 2020, 6 pages (Including English Translation).
First Office Action received for Chinese Patent Application Serial No. 201680037507.1 dated Jan. 29, 2021, 4 pages (Including English Translation).
Larman et al., "Construction of a rationally designed antibody platform for sequencing-assisted selection", PNAS, 2012, vol. 109, No. 45, pp. 18523-18528.
Notice of objection received in Israeli Patent Application Serial No. 255217 dated Aug. 31, 2020, 8 pages (Including English Translation).
Notice of Allowance received for Canadian Patent Application Serial No. 2,988,388 dated May 5, 2022, 1 page.
Notice of Reasons for Refusal received for Japanese Patent Application Serial No. 2021-072238 dated May 31, 2022, 3 pages. (Including English Translation).

* cited by examiner

CANCER NEOEPITOPES

This application claims priority to our U.S. Provisional Application Ser. No. 62/178,956, filed Apr. 23, 2015, and to our U.S. Provisional Application Ser. No. 62/159,145, filed May 8, 2015, both of which are incorporated by reference herein.

FIELD OF THE INVENTION

The field of the invention is cancer neoepitopes, and especially identification and use of neoepitopes in the production of neoepitope specific antibodies, and use of neoepitopes and neoepitope specific antibodies in prophylaxis and therapy.

BACKGROUND OF THE INVENTION

The background description includes information that may be useful in understanding the present invention. It is not an admission that any of the information provided herein is prior art or relevant to the presently claimed invention, or that any publication specifically or implicitly referenced is prior art.

It is well known in the art that most, if not all neoplastic diseases are accompanied by a relatively large number of mutations, including point mutations, insertions, deletions, and translocations. Thus, it is at least conceptually reasonable to assume that neoplastic cells may also be characterizable by the presence of one or more mutated proteins. More recently, as a result of numerous research efforts, a fairly small collection of T cell defined human tumor antigens has become available (see e.g., *Cancer Immunity* (15 Jul. 2013) Vol. 13, p. 15) for a limited number of tumor types. Unfortunately, these antigens have not resulted in an effective therapeutic agent for a particular tumor type. All publications cited herein are incorporated by reference to the same extent as if each individual publication or patent application were specifically and individually indicated to be incorporated by reference. Further, where a definition or use of a term in an incorporated reference is inconsistent or contrary to the definition of that term provided herein, the definition of that term provided herein applies and the definition of that term in the reference does not apply.

Among other possible reasons for failure to produce an immunotherapeutic agent for a specific tumor, the apparent random distribution of mutations in most tumors among different patients diagnosed with the same tumor type has severely complicated the quest to identify one or more antigens that can be used as an immunologically effective agent. Moreover, as the immune response to a particular antigen is also dependent on an individual's capacity to bind and display the antigen via the HLA complex, the statistical probability of identifying a suitable antigen for treatment of a tumor in multiple patients is very low. Thus, identification of patient specific tumor antigens is at least conceptually more likely to potentially lead to a therapeutic agent.

Unfortunately, as many tumors have developed various immune evading mechanisms, potentially useful patient and tumor-specific antigens typically fail to elicit a therapeutically effective immune response, or even production of antibodies that would bind to the patient and tumor-specific antigen. Moreover, even if a patient would have generated B cells that produce antibodies with specificity against the patient and tumor-specific antigen, isolation of such B cells is rather complex and time consuming. Likewise, isolation of therapeutically useful quantities of antibodies from such patients is equally cumbersome and time consuming and will likely exceed a patient's expected life span. In addition, even if one would be able to obtain sufficient quantities of antibodies against one patient- and tumor-specific antigen, the heterogeneity of many tumors may still render treatment ineffective as not all cells in the tumor mass may express the same antigen. Still further, even if one could produce or isolate different therapeutic antibodies from a mammal for use in a single patient, such approach would be entirely unsuitable as a mass production platform for the large amount of patients in need for immune therapy. Indeed, conventional production of monoclonal antibodies against a single antigen will often take many months.

Thus, even though antibody production is generally well known in the art, there is still a need for systems and methods that allow for rapid identification of patient-specific antigens of a tumor and accelerated production of antibodies targeting such antigens for diagnostic or therapeutic use.

SUMMARY OF THE INVENTION

The inventive subject matter is directed to identification and use of various cancer neoepitopes in a patient, particularly where such neoepitopes have not elicited a protective immune response in the patient.

In one aspect of the inventive subject matter, method of generating a pharmaceutical agent for cancer immune therapy. Especially preferred methods include a step of using matched normal omics data of a tumor to generate in silico a plurality of n-mers that contain at least one patient- and cancer-specific cancer neoepitope, and a further step of filtering in silico the n-mers to so obtain a subset of neoepitope sequences. In yet another step, at least one synthetic n-mer peptide is prepared using sequence information from the subset of neoepitope sequences, and the synthetic n-mer peptide is then employed to isolate a recombinant antibody. Sequence information of the complementarity determining region of the recombinant antibody is obtained and a synthetic antibody is generated using the sequence information of the complementarity determining region of the recombinant antibody. In still another step, the synthetic antibody may then be coupled to a therapeutic or diagnostic agent to so obtain the pharmaceutical agent.

It is generally contemplated that the matched normal omics data are whole genomic sequencing data, exome sequencing data, and/or transcriptome data, and that the matched normal omics data are matched against normal before treatment of the patient. Moreover, it is contemplated that each of the plurality of n-mer peptides has a length of between 7 and 11 amino acids, and/or that the plurality of n-mer peptides is at least 1,000 n-mer peptides. Most typically, different of the plurality of n-mer peptides have different neoepitopes. While not limiting the inventive subject matter, it is further contemplated that the step of filtering includes filtering by type of mutation, filtering by strength of expression, filtering by sub-cellular location, and/or filtering by binding affinity towards an HLA-type of the patient.

Additionally, it is contemplated that the step of using the synthetic n-mer peptide to isolate the recombinant antibody comprises phage panning, which may further comprise a step of affinity maturation. It is also contemplated that the sequence information of the complementarity determining region of the recombinant antibody comprises CDR1-H, CDR2-H, and CDR3-H, and optionally CDR1-L, CDR2-L, and CDR3-L, and/or that the synthetic antibody is generated using CDR or SDR grafting onto a human antibody scaffold.

Contemplated synthetic antibodies are typically generated via recombinant expression as a IgG, a F(ab')2, a Fab', a Fab, or a scFv, and contemplated therapeutic or diagnostic agents include non-cellular agents (e.g., chemotherapeutic drug, radio isotope, PET detectable isotope, SPECT detectable isotope, affinity agent, etc) and immune competent cells (e.g., T-cell, NK cell, etc.). For example, where the cell is a T-cell, the T cell may express a chimeric receptor having a scFv as ectodomain wherein the synthetic antibody is the scFv. Alternatively, or additionally, where the cell is an NK cell, the NK cell may express a high-affinity Fcγ receptor (CD16) and the synthetic antibody may then be an IgG that is bound to the NK cell via the high-affinity Fcγ receptor. Most notably, it should therefore be recognized that patient- and cancer-specific antibodies and compositions comprising such antibodies can be prepared in a remarkably short time (e.g., less than 8 weeks, or less than 6 weeks, or even less than 4 weeks), even in cases where the patient does not mount an effective and protective immune response to the neoepitope.

Therefore, the inventors also contemplate a method of generating a synthetic antibody to a cancer neoepitope of a patient where the cancer neoepitope failed to elicit a protective immune response. Contemplated methods will typically include a step of using the cancer neoepitope (typically fully synthetic) to select a binding recombinant antibody from a library of recombinant antibodies, wherein the cancer neoepitope is patient- and cancer-specific. In another step, hypervariable loops are then analyzed in the binding recombinant antibody to thereby obtain specificity information for the binding recombinant antibody, and a gene coding for at least a portion of a human antibody is modified using the specificity information. Finally, the gene is then recombinantly expressed to produce the synthetic antibody. Most notably, a cancer and patient specific antibody is thusly produced without use of a mammalian immune system.

In especially contemplated methods, the cancer neoepitope is an HLA matched cancer neoepitope, and/or the library of recombinant antibodies is a phage display library. Where desired, the method may further include a step of affinity maturing the binding recombinant antibody to derive an optimized binding recombinant antibody. Regardless of additional steps, the hypervariable loops are preferably analyzed by sequencing the DNA that encodes the hypervariable loops, and the step of modifying will preferably comprise CDR or SDR grafting (e.g., where the portion of the human antibody is a scFv). Recombinant expression of the modified gene will then result in the synthetic antibody in form of a IgG, a F(ab')2, a Fab', a Fab, or a scFv. Most typically, the cancer neoepitope is expressed in the cancer of the patient, and/or the neoepitope is unique to the patient and cancer in the patient.

Viewed from another perspective, the inventors therefore also contemplate a composition that comprises a synthetic antibody having binding affinity against a patient- and cancer-specific HLA-matched cancer neoepitope wherein the neoepitope is unique to the patient and cancer in the patient.

In especially preferred aspects, the HLA-matched cancer neoepitope is matched for MHC-I presentation, and the synthetic antibody is selected from the group consisting of an IgG, a F(ab')2, a Fab', a Fab, and a scFv. Where desired, the therapeutic agent may be coupled to the synthetic antibody and the therapeutic agent is a non-cellular agent (e.g., chemotherapeutic drug, radio isotope, PET detectable isotope, SPECT detectable isotope, or affinity agent). Alternatively, the therapeutic agent may also be a cell, and especially an immune competent cell (e.g., T-cell or an NK cell). For example, where the cell is a T-cell, it may express a chimeric receptor having a scFv as ectodomain wherein the synthetic antibody is the scFv. On the other hand, where the cell is an NK cell, it may express a high-affinity Fcγ receptor (CD16) wherein the synthetic antibody is an IgG that is bound to the NK cell via the high-affinity Fcγ receptor. Among other compositions, contemplated cancer neoepitope may have a sequence selected from the group consisting of SEQ ID NO 1 to SEQ ID NO 1,408,729.

In yet another aspect of the inventive subject matter, the inventors also contemplate a composition that comprises a solid phase to which is bound a patient- and cancer-specific HLA-matched cancer neoepitope, wherein the cancer neoepitope is unique to the patient and cancer in the patient. For example, suitable solid phases will include a wall of a reagent container, a magnetic bead, or an individually addressable element, and especially preferred cancer neoepitopes will have a length of between 7 and 9 amino acids. Among other neoepitopes, contemplated neoepitopes include those having a sequence according to any one of SEQ ID NO 1 to SEQ ID NO 1,408,729. Where desired, it is contemplated that a synthetic antibody (e.g., IgG, a F(ab')2, a Fab', a Fab, and a scFv) is bound to the cancer neoepitope, which may be in turn be coupled to a virus particle.

Various objects, features, aspects and advantages of the inventive subject matter will become more apparent from the following detailed description of preferred embodiments, along with the accompanying drawing figures in which like numerals represent like components.

DETAILED DESCRIPTION

The inventors have discovered that various diagnostic and therapeutic compositions and agents can be prepared in a conceptually simple but effective approach that combines in silico and in vitro techniques.

Using the inventors' systems and methods, it should now be appreciated that entirely synthetic antibodies against one or more patient specific neoepitopes can be generated, and particularly against antigens that have either not elicited a protective immune response and/or against antigens that exhibited a suppressed immune response. Even more advantageously, it should be noted that such synthetic antibodies can be prepared by in silico analysis of omics data of a patient to so derive a relatively large number of potentially useful neoepitopes that can then be further filtered to increase therapeutic efficacy. Viewed from another perspective, contemplated synthetic monoclonal antibodies are prepared without actual time consuming isolation of tumor specific peptides from the tumor and without any immunization procedure in a mammal (or other animal with immune system). Still further, it should be noted that the methods contemplated herein will allow for fast production of synthetic antibodies, typically within several days to several weeks (e.g., between 5 and 21 days).

Figure 1:
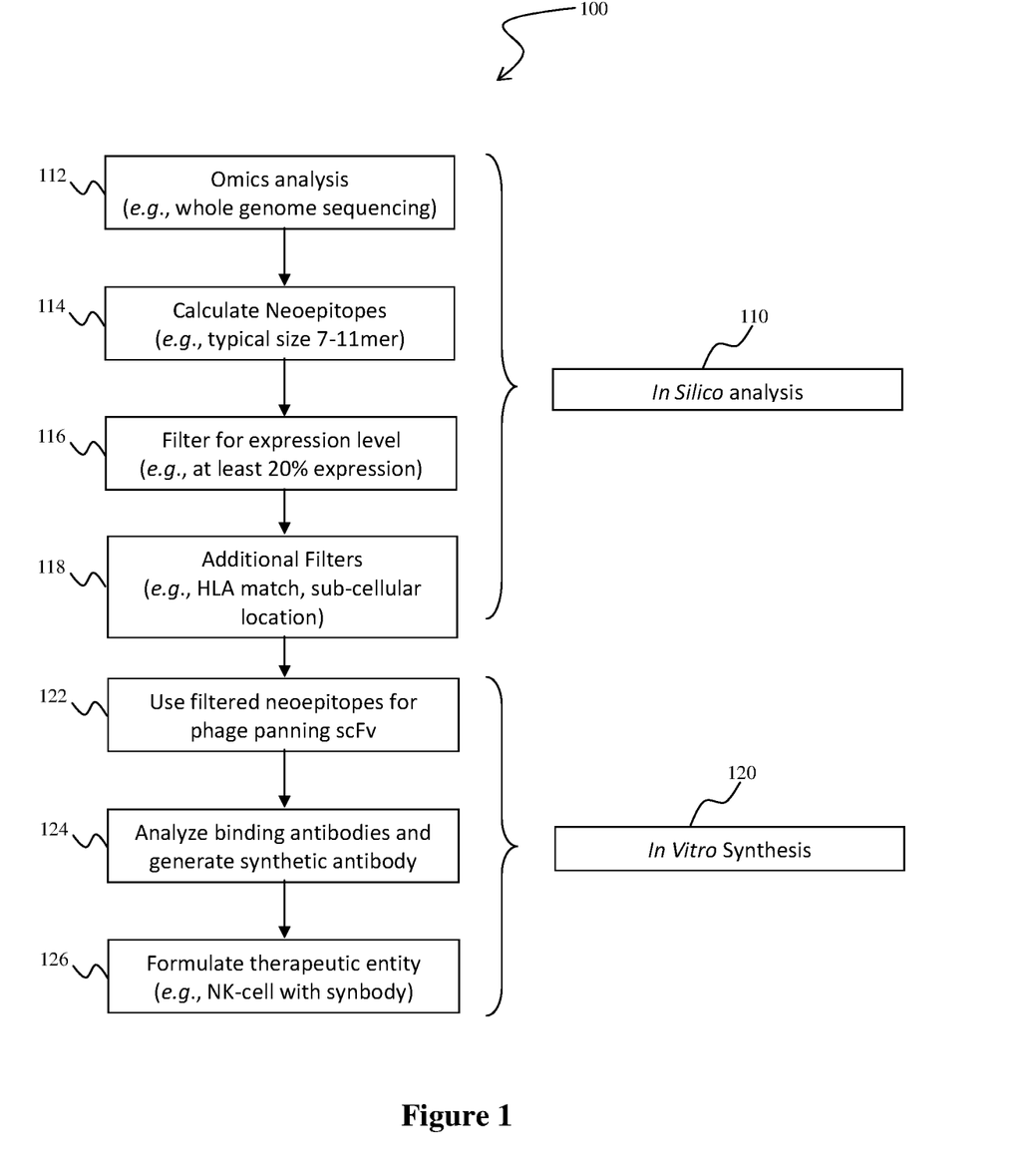
FIG. 1 is an exemplary schematic flow diagram of one aspect of the inventive subject matter.
Figure 2:
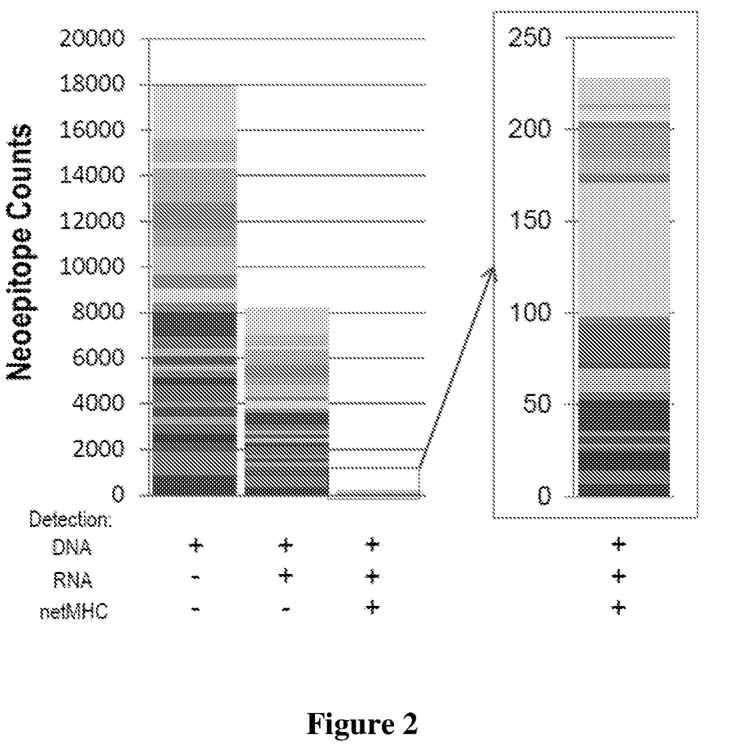
FIG. 2 is an exemplary plot depicting filtering outcomes for calculated neoepitopes.

Briefly, and as exemplarily illustrated in the flow chart of FIG. 1, one contemplated method 100 will comprise an in silico analysis portion 110 and an in vitro synthesis portion 120. Most typically, the in silico analysis commences with an omics analysis 112 to identify mutations in the tumor relative to normal tissue of the same patient, and a step of calculation of one or more neoepitopes 114 is performed to define neoepitopes that are specific to the tumor and patient. So obtained neoepitopes are further subjected to filtering step 116 to, for example, eliminate weakly or non-expressed neoepitopes. Identified expressed neoepitopes may then be subject to additional filtering algorithms 118, for example, to limit neoepitopes to extracellularly exposed or MHC-I bound neoepitopes. FIG. 2 exemplarily shows the outcome of a series of filtering steps. Here, whole genome sequencing analysis of a triple negative breast cancer sample against matched normal (i.e., compared against non-diseased tissue of the same patient) revealed a relatively large number (~18,000) of neoepitopes in the tumor sample. Notably, a first filtering step removed more than 50% of all of the identified neoepitopes on the basis of expression strength. Here, neoepitope sequences were removed with an expression level of less than 20% of expression as compared to the matched normal sample. The remaining sequences were subjected to an in silico analysis to determine those sequences that would bind (e.g., less than 500 nM affinity) to a single specific HLA-type of the same sample. It should be noted that once more a substantial fraction of neoepitopes was eliminated, and that ultimately only less than 1.3% of all neoepitopes were found suitable for use.

Referring again to FIG. 1, and after the in silico identification of suitable neoepitope sequences, corresponding synthetic peptides are then prepared in vitro (e.g., using solid phase synthesis) and used in a phage display assay, typically using a large diversity library (e.g., at least $10^9$ distinct members) of scFv constructs as shown in step 122. It should be appreciated that avidly binding phages will bind via a matching scFv displayed by the phage, which is encoded by the corresponding nucleic acid found in the bound phage. Sequence analysis on that phage DNA will then reveal the sequences for the complementarity determining regions (typically at least CDR1-H, CDR2-H, and CDR3-H, and CDR1-L, CDR2-L, and CDR3-L) in the scFv as shown in step 124. This information can then be used as a guide to modify a nucleic acid encoding a human or humanized scFv or other antibody. Once expressed in a suitable expression system, the synthetic antibody ('synbody') is then formulated into a desired therapeutic entity, for example, by binding the antibody to an NK cell, or grafting the corresponding scFv onto a chimeric T-cell receptor.

More particularly, and with respect to obtaining omics information from the patient to identify one or more neoepitopes it is generally contemplated that the omics data are obtained from one or more patient biopsy samples following standard tissue processing protocol and sequencing protocols. While not limiting to the inventive subject matter, it is typically preferred that the data are patient matched tumor data (e.g., tumor versus same patient normal), and that the data format is in SAM, BAM, GAR, or VCF format. However, non-matched or matched versus other reference (e.g., prior same patient normal or prior same patient tumor, or homo statisticus) are also deemed suitable for use herein. Therefore, the omics data may be 'fresh' omics data or omics data that were obtained from a prior procedure (or even different patient). For example, neoepitopes may be identified from a patient tumor in a first step by whole genome and/or exome analysis of a tumor biopsy (or lymph biopsy or biopsy of a metastatic site) and matched normal tissue (i.e., non-diseased tissue from the same patient such as peripheral blood) via location-guided synchronous comparison of the so obtained omics information.

Among other options, it is contemplated that genomic analysis can be performed by any number of analytic methods, however, especially preferred analytic methods include WGS (whole genome sequencing) and exome sequencing of both tumor and matched normal sample using next generation sequencing such as massively parallel sequencing methods, ion torrent sequencing, pyrosequencing, etc. Likewise, it should be appreciated that computational analysis of the sequence data may be performed in numerous manners. In most preferred methods, however, analysis is performed in silico by location-guided synchronous alignment of tumor and normal samples as, for example, disclosed in US 2012/0059670A1 and US 2012/0066001A1 using BAM files and BAM servers. Of course, alternative file formats for sequence analysis (e.g., SAM, GAR, FASTA, etc.) are also expressly contemplated herein.

It should be noted that any language directed to a computer should be read to include any suitable combination of computing devices, including servers, interfaces, systems, databases, agents, peers, engines, controllers, or other types of computing devices operating individually or collectively. One should appreciate the computing devices comprise a processor configured to execute software instructions stored on a tangible, non-transitory computer readable storage medium (e.g., hard drive, solid state drive, RAM, flash, ROM, etc.). The software instructions preferably configure the computing device to provide the roles, responsibilities, or other functionality as discussed below with respect to the disclosed apparatus. Further, the disclosed technologies can be embodied as a computer program product that includes a non-transitory computer readable medium storing software instructions that causes a processor to execute the disclosed steps associated with implementations of computer-based algorithms, processes, methods, or other instructions. In especially preferred embodiments, the various servers, systems, databases, or interfaces exchange data using standardized protocols or algorithms, possibly based on HTTP, HTTPS, AES, public-private key exchanges, web service APIs, known financial transaction protocols, or other electronic information exchanging methods. Data exchanges among devices can be conducted over a packet-switched network, the Internet, LAN, WAN, VPN, or other type of packet switched network; a circuit switched network; cell switched network; or other type of network.

Of course, it should be appreciated that downstream analysis may be performed on the so identified sequence differences to identify those that lead to a new peptide sequence based on the cancer and patient specific mutation. Neoepitopes may therefore be identified by considering the type (e.g., deletion, insertion, transversion, transition, translocation) and impact of the mutation (e.g., non-sense, missense, frame shift, etc.), and may as such serve as a content filter through which silent and other non-relevant (e.g., non-expressed) mutations are eliminated.

It should further be appreciated that neoepitope sequences as contemplated herein can be defined as sequence stretches with relatively short length (e.g., 5-30 mers, more typically 7-11 mers, or 12-25 mers) wherein such stretches include the change(s) in the amino acid sequences. Most typically, the change(s) is/are located centrally or near the center (e.g., less than 4, or less than 5, or less than 6 amino acids from center position). Therefore, and viewed from a different perspective, neoepitope sequences contemplated herein will especially include those in which a single amino acid is exchanged relative to the matched normal sequence, and in which the position of the changed amino acid is centrally located, or near the center of the neoepitope sequence (e.g., in a 9-mer, the changed amino acid is at position 2, 3, 4, or 5, and more typically at position 3, 4, or 5, and most typically at position 4 or 5). Thus, it should be appreciated that a single amino acid change may be presented in numerous neoepitope sequences that include the changed amino acid, depending on the position of the changed amino acid. Advantageously, such sequence variability allows for multiple choices of neoepitopes and so increases the number of potentially useful targets that can then be selected on the basis of one or more desirable traits (e.g., highest affinity to a patient HLA-type, highest structural stability, etc.). Most typically, neoepitopes will be calculated to have a length of between 2-50 amino acids, more typically between 5-30 amino acids, and most typically between 9-15 amino acids, with a changed amino acid preferably centrally located or otherwise situated in a manner that improves its binding to MHC. For example, where the epitope is to be presented by the MHC-I complex, a typical epitope length will be about 8-11 amino acids, while the typical epitope length for presentation via MHC-II complex will have a length of about 13-17 amino acids. As will be readily appreciated, since the position of the changed amino acid in the neoepitope may be other than central, the actual peptide sequence and with that actual topology of the neoepitope may vary considerably. Moreover, where the neoepitope is presented to an immune competent (or other) cell as a synthetic peptide, it should be appreciated that the synthetic peptide may be significantly longer than the peptide portion that is ultimately bound by the MHC-I or MHC-II system to so allow for proteolytic processing in the cell. For example, contemplated synthetic peptides may therefore have between 8 and 15 amino acids upstream and downstream of the changed amino acid.

With respect to filtering identified neoepitopes, it is generally contemplated that neoepitopes are especially suitable for use herein where omics (o other) analysis reveals that the neoepitope is actually expressed. Identification of expression and expression level of a neoepitope can be performed in all manners known in the art and preferred methods include quantitative RNA (hnRNA or mRNA) analysis and/or quantitative proteomics analysis. Most typically, the threshold level for inclusion of neoepitopes will be an expression level of at least 20%, and more typically at least 50% of expression level of the corresponding matched normal sequence, thus ensuring that the (neo)epitope is at least potentially 'visible' to the immune system. Consequently, it is generally preferred that the omics analysis also includes an analysis of gene expression (transcriptomic analysis) to so help identify the level of expression for the gene with a mutation. There are numerous methods of transcriptomic analysis know in the art, and all of the known methods are deemed suitable for use herein. For example, preferred materials include mRNA and primary transcripts (hnRNA), and RNA sequence information may be obtained from reverse transcribed polyA$^+$-RNA, which is in turn obtained from a tumor sample and a matched normal (healthy) sample of the same patient. Likewise, it should be noted that while polyA$^+$-RNA is typically preferred as a representation of the transcriptome, other forms of RNA (hn-RNA, non-polyadenylated RNA, siRNA, miRNA, etc.) are also deemed suitable for use herein. Preferred methods include quantitative RNA (hnRNA or mRNA) analysis and/or quantitative proteomics analysis. Most typically, RNA quantification and sequencing is performed using qPCR and/or rtPCR based methods, although other methods (e.g., solid phase hybridization-based methods) are also deemed suitable. Viewed from another perspective, transcriptomic analysis may be suitable (alone or in combination with genomic analysis) to identify and quantify genes having a cancer and patient specific mutation.

Similarly, proteomics analysis can be performed in numerous manners to ascertain expression of the neoepitope, and all known manners or proteomics analysis are contemplated herein. However, particularly preferred proteomics methods include antibody-based methods and mass spectroscopic methods. Moreover, it should be noted that the proteomics analysis may not only provide qualitative or quantitative information about the protein per se, but may also include protein activity data where the protein has catalytic or other functional activity. One example of technique for conducting proteomic assays includes U.S. Pat. No. 7,473,532 to Darfler et al. titled "Liquid Tissue Preparation from Histopathologically Processed Biological Samples, Tissues, and Cells" filed on Mar. 10, 2004.

In addition, neoepitopes may also be subject to detailed analysis and filtering using predefined structural and/or sub-cellular location parameters. For example, it is contemplated that neoepitope sequences are selected for further use if they are identified as having a membrane associated location (e.g., are located at the outside of a cell membrane of a cell) and/or if in silico structural calculation confirms that the neoepitope is likely to be solvent exposed or presents a structurally stable epitope, etc.

Consequently, it should be recognized that patient and cancer specific neoepitopes can be identified from omics information in an exclusively in silico environment that ultimately predicts potential epitopes that are unique to the patient and tumor type. So identified and selected neoepitopes can then be further filtered in silico against an identified patient HLA-type. Such HLA-matching is thought to ensure strong binding of the neoepitopes to the MHC-I complex of nucleated cells and the MHC-II complex of specific antigen presenting cells. Targeting both antigen presentation systems is particularly thought to produce a therapeutically effective and durable immune response involving both, the cellular and the humoral branch of the immune system. Of course, it should also be appreciated that thusly identified HLA-matched neoepitopes can be biochemically validated in vitro.

HLA determination for both MHC-I and MHC-II can be done using various methods in wet-chemistry that are well known in the art, and all of these methods are deemed suitable for use herein. However, in especially preferred methods, the HLA-type can also be predicted from omics data in silico using a reference sequence containing most or all of the known and/or common HLA-types as is shown in more detail below. In short, a patient's HLA-type is ascertained (using wet chemistry or in silico determination), and a structural solution for the HLA-type is calculated or obtained from a database, which is then used as a docking model in silico to determine binding affinity of the neoepitope to the HLA structural solution. Suitable systems for determination of binding affinities include the NetMHC platform (see e.g., Nucleic Acids Res. 2008 Jul. 1; 36 (Web Server issue): W509-W512.), HLAMatchmaker (http://www.epitopes.net/downloads.html), and IEDB Analysis Resource (http://tools.immuneepitope.org/mhcii/). Neoepitopes with high affinity (e.g., less than 100 nM, less than 75 nM, less than 50 nM for MHC-I; less than 500 nM, less than 300 nM, less than 100 nM for MHC-II) against the previously determined HLA-type are then selected. In calculating the highest affinity, modifications to the neoepitopes may be implemented by adding N- and/or C-terminal modifications to the epitope to further increase binding of a synthetic neoepitope to the HLA-type of the patient. Thus, neoepitopes may be native as identified or further modified to better match a particular HLA-type.

In yet another aspect of filtering, the neoepitopes may be compared against a database that contains known human sequences to so avoid use of a human-identical sequence. Moreover, filtering may also include removal of neoepitope sequences that are due to SNPs in the patient. For example, The Single Nucleotide Polymorphism Database (dbSNP) is a free public archive for genetic variation within and across different species developed and hosted by the National Center for Biotechnology Information (NCBI) in collaboration with the National Human Genome Research Institute (NHGRI). Although the name of the database implies a collection of one class of polymorphisms only (i.e., single nucleotide polymorphisms (SNPs)), it in fact contains a relatively wide range of molecular variation: (1) SNPs, (2) short deletion and insertion polymorphisms (indels/DIPs), (3) microsatellite markers or short tandem repeats (STRs), (4) multinucleotide polymorphisms (MNPs), (5) heterozygous sequences, and (6) named variants. The dbSNP accepts apparently neutral polymorphisms, polymorphisms corresponding to known phenotypes, and regions of no variation. Using such database, the patient and tumor specific neoepitopes may be further filtered to remove those know sequences, yielding a therapeutic sequence set with a plurality of neoepitope sequences.

Consequently, it should be appreciated that the so identified cancer neoepitopes are unique to the patient and the particular cancer in the patient (e.g., having a frequency of less than 0.1% of all neoepitopes, and more typically less than 0.01% in a population of cancer patients diagnosed with the same cancer), but that the so identified cancer neoepitopes have a high likelihood of being presented in a tumor and therefore provide a high likelihood of being specifically targeted by a synthetic antibody, even if the cancer has an immune suppressive microenvironment.

In practice, neoepitopes can be scored/ranked based on allele frequency multiplied by the transcripts per million number to get a likelihood score. This score can then be further augmented using HLA information and calculated or actual binding affinity to the patient's HLA type. For example, an exemplary ranking format may be:
>254 NM_001000.3 RPL39 Missense p.M29K A→T Normal: WIRMKTGNK, AF: 0.179104477612 TPM: 1023.96 TPM_MEDIAN: 7.35 LL: 183.395820896 netMHC: 242.96 Allele: HLA-A0301 WIRKKTGNK.

Here, the file is a FASTA formatted file, and entries start with the '>' character, which just reports sample information. The next line is the neoepitope. In the sample information line contains a number used for indexing the sample (e.g., 254), the Refseq Gene ID (e.g., NM_001000.3), the HUGO common name (e.g., RPL39), the variant classification (e.g., Missense), the protein change (e.g., p.M29K), the base pair change (e.g., A→T), the normal epitope (e.g., Normal: WIRMKTGNK), allele frequency (e.g., AF: 0.179104477612), Transcripts per million for this gene (e.g., TPM: 1023.96), TPM_MEDIAN which is the median expression level of all the genes (e.g., TPM_MEDIAN: 7.35), the LL score which is just AF×TPM (e.g., LL: 183.395820896), the netMHC predicted binding value (e.g., netMHC: 242.96), and the specific HLA allele that the neoepitope binds to (e.g., Allele: HLA-A0301). The next line is then the neoepitope (e.g., WIRKKTGNK).

The feasibility of such approach was shown by the inventors using omics information from the publically available TCGA database covering numerous cancers, in which each of the cancers had data available for multiple patients. Table 1 below lists the name and cancer type, followed by neoepitopes found for each cancer type.

TABLE 1

| Name | Cancer Type | SEQ ID NOs. |
|---|---|---|
| BLCA | Bladder Urothelial Carcinoma | 1-35,781 |
| BRCA | Breast invasive carcinoma | 35,782-105,572 |
| CESC | Cervical squamous cell carcinoma and endocervical adenocarcinoma | 105,573-117,234 |
| COAD | Colon adenocarcinoma | 117,235-454,041 |
| DLBC | Lymphoid Neoplasm Diffuse Large B-cell Lymphoma | 454,042-461,532 |
| GBM | Glioblastoma multiforme | 461,533-470,083 |
| HNSC | Head and Neck squamous cell carcinoma | 470,084-527,237 |
| KICH | Kidney Chromophobe | 527,238-541,231 |
| KIRC | Kidney renal clear cell carcinoma | 541,232-562,123 |
| KIRP | Kidney renal papillary cell carcinoma | 562,124-570,663 |
| LAML | Acute Myeloid Leukemia | 570,664-570,775 |
| LGG | Brain Lower Grade Glioma | 570,776-573,578 |
| LIHC | Liver hepatocellular carcinoma | 573,579-607,372 |
| LUAD | Lung adenocarcinoma | 607,373-683,023 |
| LUSC | Lung squamous cell carcinoma | 683,024-770,110 |
| OV | Ovarian serous cystadenocarcinoma | 770,111-797,661 |
| PRAD | Prostate adenocarcinoma | 797,662-800,692 |
| READ | Rectum adenocarcinoma | 800,693-906,174 |
| SARC | Sarcoma | 906,175-913,860 |
| SKCM | Skin Cutaneous Melanoma | 913,861-1,089,652 |
| STAD | Stomach adenocarcinoma | 1,089,653-1,202,468 |
| THCA | Thyroid carcinoma | 1,202,469-1,208,734 |
| UCEC | Uterine Corpus Endometrial Carcinoma | 1,208,735-1,408,729 |

Thus, it should be recognized that it is feasible to assemble an entire rational-designed collection of neoepitopes of a specific patient with a specific cancer, which can then be further tested in vitro to find or generate high-affinity antibodies. Indeed, contemplated collections may include one, two, three, four, five, six-ten, 10-50, 50-150, 1,000 and even more patient- and cancer-specific neoepitopes. Viewed from a different perspective, the rational-designed collection of neoepitopes may cover between 1-10%, or between 10-25%, or between 25-60%, or between 60-100% of all neoepitopes that are expressed and bind to the HLA type of the patient. Thus, contemplated collections will comprise at least 15%, at least 25%, at least 50%, at least 70, or at least 90% of the cancer immunome (neoepitopes that are expressed and bind to the HLA type of the patient). Consequently, it should also be appreciated that even for patients with tumor immune suppression or chemotherapy-damaged immune system, numerous targets for immune therapy are now available.

To obtain a synthetic antibody against the identified neoepitope(s), it is contemplated that the in silico identified is prepared in vitro to yield a synthetic peptide. There are numerous methods known in the art to prepare synthetic peptides, and all known manners are deemed suitable for use herein. For example, peptides with cancer neoepitope sequences can be prepared on a solid phase (e.g., using Merrified synthesis), via liquid phase synthesis, or from smaller peptide fragments. In less preferred aspects, peptides could also be produced by expression of a recombinant nucleic acid in a suitable host (especially where multiple neoepitopes are on a single peptide chain, optionally with spacers between neoepitopes or cleavage sites).

Therefore, the structure of the synthetic peptides corresponding to or comprising the neoepitope sequences may be X-L$_1$-(A$_n$-L$_2$)$_m$-Q, in which X is an optional coupling group or moiety that is suitable to covalently or non-covalently attaches the synthetic peptide to a solid phase, L$_1$ is an optional linker that covalently links the synthetic peptide to a solid phase or the coupling group. A$_n$ is the synthetic peptide having the neoepitope sequence with A being a natural (proteinogenic) amino acid and n is an integer between 7 and 30, and most typically between 7 and 11 or 15-25. L$_2$ is an optional linker that may be present, especially where multiple synthetic peptide sequences (identical or different) are in the construct, and m is an integer, typically between 1 and 30, and most typically between 2 and 15. Finally, Q is a terminal group which may used to couple the end of the synthetic peptide to the solid phase (e.g., to sterically constrain the peptide) or to a reporter group (e.g., fluorescence marker) or other functional moiety (e.g., affinity marker). Consequently, it should be noted that where the synthetic peptide is used for direct MHC-I binding, the overall length will be between 8 and 10 amino acids. Similarly, where the synthetic peptide is used for direct MHC-II binding, the overall length will be between 14 and 20 amino acids. On the other hand, where the synthetic peptide is processed in the cell (typically via proteasome processing) prior to MHC presentation, the overall length will typically be between 10 and 40 amino acids, with the changed amino at or near a central position in the synthetic peptide.

For example, X could be a non-covalent affinity moiety (e.g., biotin) that binds a corresponding binding agent (e.g., avidin) on the solid phase, or a chemical group (with or without spacer) that reacts with the N- or C-terminal amino or carboxyl group of the peptide, or a selectively reactive group (e.g., iodoacetyl or maleimide group) that reacts with a sulfhydryl group in the peptide or linker L$_1$. L$_1$ may be used to increase the distance of the synthetic peptide from the solid phase and will therefore typically comprise a flexible linear moiety (e.g., comprising glycol groups, alkoxy groups, glycine, etc.) having a length of equivalent to between about 2-20 carbon-carbon bonds (e.g., between 0.3 nm and 3 nm). Of course, it should also be appreciated that the synthetic peptide may use the solid phase on which the peptide was produced and as such not require a separate coupling group or linker.

Depending on the particular synthetic peptide and coupling method, it should be appreciated that the nature of the solid phase may vary considerably, and all known solid phases for attachment of peptides are deemed suitable for use herein. For example, suitable solid phases include agarose beads, polymer beads (colored or otherwise individually addressable), wall surfaces of a well in a microtiter plate, paper, nitrocellulose, glass, etc. The person of ordinary skill in the art will be readily appraised of a suitable choice of solid phase and attachment chemistry. In further preferred aspects, it is also noted that the solid phase will generally be suitable for protocols associated with phage display methods such as to allow peptides presented on a phage (or other scaffold carrier) to reversibly bind to the solid phase via the synthetic peptide. In still further contemplated uses, it should also be recognized that the solid phase may be a carrier protein used in vaccination (e.g., albumin, KLH, tetanus toxoid, diphtheria toxin, etc.), particularly where the synthetic protein is used as a vaccine in a mammal or as an immunogenic compound in a non-human mammal for antibody production. Likewise, the synthetic protein may also be used as a vaccine or immunogenic compound without any carrier.

In still further preferred methods, it should be recognized that where the synthetic peptide (that comprises or corresponds to the cancer neoepitope) is immobilized on a solid phase, affinity agents, and particularly antibodies, to the neoepitope may be isolated and/or refined. Most preferably, such isolation will include a prefabricated high-diversity library of antibodies. As used herein, and unless the context dictates otherwise, the term "antibody" or "antibodies" includes all isotypes and subtypes of antibodies (e.g., IgG, IgM, IgE, etc.) as well as all fragments thereof, including monovalent IgG, F(ab')$_2$, Fab', Fab, scFv, scFv-Fc, VhH, etc. Moreover, contemplated antibodies may be humanized, of human or non-human (e.g., rodent) origin, or may be chimeric. In a typical method, a high-diversity library may be a phage display library having a diversity of at least $10^9$ diverse members, or at least $10^{10}$ diverse members, or even higher, typically based on M13 phages and display via pIII, pVIII, pVI, or pIX, or based on T7 phages and the gene 10 capsid protein. As should be readily appreciated, use of large diversity libraries will provide in relatively short time several binding candidate antibodies that can be further selected for best binders. Indeed, where binding affinity to the immobilized synthetic peptide is less than desired, it should be recognized that affinity can be improved via affinity maturation using protocols well known in the art. For example, low affinity (K$_D$>10$^{-7}$M) binders or members of smaller libraries may be subjected to affinity maturation to improve binding affinity and/or kinetic using methods well known in the art (see e.g., *Briefings In Functional Genomics And Proteomics*. Vol 1. No 2. 189-203. July 2002). In addition, it should be noted that while antibody libraries are generally preferred, other scaffolds are also deemed suitable and include beta barrels, ribosome display, cell surface display, etc. (see e.g., *Protein Sci.* 2006 January; 15(1): 14-27.) Thus, it should be appreciated that in preferred aspects the synthetic peptide is used as a bait in a library of antibodies to so identify high-affinity binding (K$_D$<10$^{-7}$M, and more typically K$_D$<10$^{-8}$M) antibodies.

As the antibodies are directly coupled to the cell that carries the nucleic acid encoding these antibodies, it should be further appreciated that such nucleic acid can then be analyzed to identify sequence elements encoding the hypervariable loops, the CDR1, CDR2, and CDR3, for light and heavy chain, respectively, and/or SDRs (specificity determining residues). Most typically, determination is performed using standard sequencing methods. Once determined, it is then contemplated that the hypervariable loops, or the CDR1-H, CDR2-H, and/or CDR3-H and/or the CDR1-L, CDR2-L, and/or CDR3-L, and/or SDRs are grafted onto a human or humanized antibody scaffold or antibody. As will be readily appreciated, grafting can be done by genetic engineering of a nucleic acid that encodes the human or humanized antibody scaffold or antibody. For example, within each CDR, there are more variable positions that are directly involved in the interaction with antigen, i.e., specificity-determining residues (SDRs), whereas there are more conserved residues that maintain the conformations of CDRs loops. SDRs may be identified from the 3D structure of the antigen-antibody complex and/or the mutational analysis of the CDRs. An SDR-grafted humanized antibody is constructed by grafting the SDRs and the residues maintaining the conformations of the CDRs onto human template. Consequently, it should be recognized that human or humanized antibodies with specificity to cancer neoepitopes can be prepared in an entirely synthetic manner in which the antibody is expressed in a cell that has not previously contacted the antigen. Moreover, contemplated methods allow production of patient and cancer specific antibodies for treatment of a patient that has failed to produce or effectively use antibodies against the neoepitopes.

While not limiting to the inventive subject matter, so prepared synthetic antibodies can be used directly as an IgG (or other isotype), as a fragment (e.g., bispecific Fab or other bispecific fragment), and/or as a chimeric protein (e.g., scFv as ectodomain in a chimeric T cell receptor), alone or in conjugation with a therapeutic or diagnostic agent, and/or as a hybrid protein with a transmembrane domain to ensure membrane anchoring of the antibody to a cell. Consequently, the inventors contemplate a method of generating a pharmaceutical agent for cancer immune therapy in which the so identified synthetic antibodies are coupled to a therapeutic or diagnostic agent (which may have a cellular or non-cellular component) to so obtain the pharmaceutical agent.

For example, contemplated non-cellular agents include various chemotherapeutic drugs to so deliver the chemotherapeutic drug directly to a cancer cell. For example, suitable chemotherapeutic drugs include kinase inhibitors (e.g., erlotinib, imatinib, bortezomib, etc.), topoisomerase inhibitors (e.g., topotecan, etoposide, teniposide, etc.), nucleotide analogs (e.g., fluorouracil, gemcitabine, azacytidine, etc.), platinum based agents (e.g., cisplatin, carboplatin, etc.), alkylating agents (e.g., cyclophosphamide, chlorambucil, temozolomide, etc.), taxanes (e.g., docetaxel, paclitaxel, etc.), microtubulin inhibitors (e.g., vincristine, vinblastine, etc.). On the other hand, directed and site specific radiotherapy may be employed by coupling a radiologic agent to the antibody to selectively destroy a cancer cell. Suitable radiologic agents include all agents suitable for brachytherapy, and especially $^{125}$I, $^{103}$Pd, or $^{192}$Ir. Alternatively, $^{10}$B may be used where neutron capture therapy with low-energy thermal neutrons is desired. Likewise, imaging agents may be coupled to the antibody or fragment thereof, and especially preferred imaging agents include PET (e.g., $^{11}$C, $^{13}$N, $^{15}$O, and $^{18}$F) and SPECT labels (e.g., $^{123}$I, $^{99m}$Tc, $^{133}$Xe, $^{201}$Tl, and $^{18}$F). As used herein, and unless the context dictates otherwise, the term "coupled to" is intended to include both direct coupling (in which two elements that are coupled to each other contact each other) and indirect coupling (in which at least one additional element is located between the two elements). Therefore, the terms "coupled to" and "coupled with" are used synonymously. In still further contemplated aspects, the antibody may be modified with an antigen that is known to be an immunogenic antigen. Such modification is particularly advantageous where the patient was previously immunized with the same antigen. In such scenario, it is contemplated that the cancer cells with the neoepitopes are 'painted' with the modified antibody presenting the immunogenic antigen, which is particularly advantageous where an immune response to the original neoepitope was not immunogenic or suppressed.

Where the neoepitopes are employed to target immune cells to a tumor, it should be noted that the antibody may also be coupled to a portion of a T-cell receptor or a cytotoxic T-cell or an NK cell. For example, where the antibody is used in a chimeric T-cell receptor of a cytotoxic T-cell, the antigen binding portion of the chimeric T-cell receptor may have a scFv as ectodomain and the scFv has binding affinity against one of the neoepitopes (e.g., those of SEQ ID NO:1-SEQ ID NO:1,408,729). On the other hand, where the antibody is used with an NK cell, preferred NK cells are NK-92 derivatives that are modified to have a reduced or abolished expression of at least one killer cell immunoglobulin-like receptor (KIR), which will render such cells constitutively activated (via lack of or reduced inhibition). Such NK cells may be obtained from NantKwest (see nantkwest.com) as aNK cells ('activated natural killer cells) and may be further modified to express a membrane bound synthetic antibody with binding affinity to a neoepitope (e.g., those of SEQ ID NO:1-SEQ ID NO:1,408,729).

Alternatively, the NK cell may also be a NK-92 derivative that is modified to express the high-affinity Fcγ receptor (CD16), and it is especially contemplated that the antibodies contemplated herein may be bound to such modified NK cells. Such cells may be obtained from NantKwest as haNK cells ('high-affinity natural killer cells). Likewise, the NK cell may also be genetically engineered to express a chimeric T-cell receptor. In especially preferred aspects, the chimeric T-cell receptor will have an scFv portion or other ectodomain with binding specificity against a neoepitope (e.g., SEQ ID NO:1-SEQ ID NO:1,408,729). Of course, it should also be noted that where the therapeutic agent has a cellular component, the cell may be an autologous cell from the patient or a heterologous cell.

Consequently, it should be recognized that an effective immune response against a cancer neoepitope may be elicited using a process that does not require immunization in the patient or other organism, reducing dramatically response time and availability of therapeutic antibodies. Indeed, using contemplated compositions and methods allows to stimulate or even produce an immune response against a neoepitope in a patient where the immune system of that patient was not sufficient to generate a protective response (e.g., due to chemotherapy or immune suppression by the tumor or Tregs or myeloid-derived suppressor cells).

Depending on the particular composition, it should therefore be appreciated that the pharmaceutical agent may be administered to a patient in vivo or a cell or tissue in vitro. For example, where the synthetic antibody is used in diagnosis, the antibody may be added to a tissue sample ex vivo. (e.g., on a microscope slide to a FFPE sample using a fluorescence labeled antibody) or in vivo (e.g., where the antibody is labeled with a PET label). On the other hand, where the antibody is bound to an immune competent cell, the antibody may be administered to a patient in vivo.

In some embodiments, the numbers expressing quantities of ingredients, properties such as concentration, reaction conditions, and so forth, used to describe and claim certain embodiments of the invention are to be understood as being modified in some instances by the term "about." Accordingly, in some embodiments, the numerical parameters set forth in the written description and attached claims are approximations that can vary depending upon the desired properties sought to be obtained by a particular embodiment. In some embodiments, the numerical parameters should be construed in light of the number of reported significant digits and by applying ordinary rounding techniques. Notwithstanding that the numerical ranges and parameters setting forth the broad scope of some embodiments of the invention are approximations, the numerical values set forth in the specific examples are reported as precisely as practicable. Unless the context dictates the contrary, all ranges set forth herein should be interpreted as being inclusive of their endpoints, and open-ended ranges should be interpreted to include commercially practical values. Similarly, all lists of values should be considered as inclusive of intermediate values unless the context indicates the contrary.

It should be apparent to those skilled in the art that many more modifications besides those already described are possible without departing from the inventive concepts herein. The inventive subject matter, therefore, is not to be

SEQUENCE LISTING

The patent contains a lengthy "Sequence Listing" section. A copy of the "Sequence Listing" is available in electronic form from the USPTO web site (https://seqdata.uspto.gov/?pageRequest=docDetail&DocID=US11421016B2). An electronic copy of the "Sequence Listing" will also be available from the USPTO upon request and payment of the fee set forth in 37 CFR 1.19(b)(3).

What is claimed is:

1. A method of generating a pharmaceutical agent for cancer immune therapy, comprising:
    using matched normal omics data of a tumor to generate in silico a plurality of n-mers that contain at least one patient- and cancer-specific cancer neoepitope wherein the omics data from each of the tumor and the matched patient normal sample include data selected from the group consisting of whole genomic sequencing data, exome sequencing data, transcriptome data, and combinations thereof;
    filtering in silico the n-mers to so obtain a subset of neoepitope sequences wherein the filtering is filtering by type of mutation, filtering by strength of expression, filtering by subcellular location, and/or filtering by binding affinity towards an HLA-type of the patient;
    preparing at least one synthetic n-mer peptide using sequence information from the subset of neoepitope sequences;
    using the synthetic n-mer peptide to isolate a recombinant antibody;
    obtaining sequence information of the complementarity determining region of the recombinant antibody;
    generating a synthetic antibody using the sequence information of the complementarity determining region of the recombinant antibody; and
    coupling the synthetic antibody to a therapeutic or diagnostic agent to so obtain the pharmaceutical agent.

2. The method of claim 1 wherein the matched normal omics data are matched against normal before treatment of the patient.

3. The method of claim 1 wherein each of the plurality of n-mer peptides has a length of between 7 and 11 amino acids.

4. The method of claim 1 wherein the plurality of n-mer peptides is at least 1,000 n-mer peptides.

5. The method of claim 1 wherein different of the plurality of n-mer peptides have different neoepitopes.

6. The method of claim 1 wherein the step of filtering includes at least two of filtering by type of mutation, filtering by strength of expression, filtering by sub-cellular location, and filtering by binding affinity towards an HLA-type of the patient.

7. The method of claim 1 wherein the step of using the synthetic n-mer peptide to isolate the recombinant antibody comprises phage panning.

8. The method of claim 7 wherein the step of phage panning further comprises affinity maturation.

9. The method of claim 1 wherein the sequence information of the complementarity determining region of the recombinant antibody comprises CDR1-H, CDR2-H, and CDR3-H.

10. The method of claim 1 wherein the synthetic antibody is generated using CDR or SDR grafting onto a human antibody scaffold.

11. The method of claim 1 wherein the synthetic antibody is generated via recombinant expression as a IgG, a F(ab')2, a Fab', a Fab, or a scFv.

12. The method of claim 1 wherein the therapeutic or diagnostic agent is a non-cellular agent.

13. The method of claim 12 wherein the non-cellular agent is a chemotherapeutic drug, a radio isotope, a PET detectable isotope, a SPECT detectable isotope, or an affinity agent.

14. The method of claim 1 wherein the therapeutic agent is a cell.

15. The method of claim 14 wherein the cell is a T-cell or an NK cell.

16. The method of claim 15 wherein the cell is a T-cell expressing a chimeric receptor having a scFv as ectodomain and wherein the synthetic antibody is the scFv.

17. The method of claim 15 wherein the cell is an NK cell expressing a high-affinity Fcγ receptor (CD16) and wherein the synthetic antibody is an IgG and is bound to the NK cell via the high-affinity Fcγ receptor.

* * * * *